US010846928B2

(12) United States Patent
Alterovitz et al.

(10) Patent No.: US 10,846,928 B2
(45) Date of Patent: Nov. 24, 2020

(54) METHODS, SYSTEMS, AND COMPUTER READABLE MEDIA FOR CONTROLLING A CONCENTRIC TUBE PROBE (71) Applicants: The University of North Carolina at Chapel Hill, Chapel Hill, NC (US); Vanderbilt University, Nashville, TN (US)

(72) Inventors: Ron Alterovitz, Chapel Hill, NC (US); Luis Guillermo Torres, Carrboro, NC (US); Philip Joseph Swaney, Nashville, TN (US); Hunter Bryant Gilbert, Nashville, TN (US); Robert James Webster, Nashville, TN (US); Richard Joseph Hendrick, Nashville, TN (US)

(73) Assignees: UNIVERSITY OF NORTH CAROLINA AT CHAPEL HILL, Chapel Hill, NC (US); VANDERBILT UNIVERSITY, Nashville, TN (US)

( * ) Notice: Subject to any disclaimer, the term of this patent is extended or adjusted under 35 U.S.C. 154(b) by 408 days.

(21) Appl. No.: 15/576,619

(22) PCT Filed: May 23, 2016

(86) PCT No.: PCT/US2016/033767
§ 371 (c)(1),
(2) Date: Nov. 22, 2017

(87) PCT Pub. No.: WO2016/191364
PCT Pub. Date: Dec. 1, 2016

(65) Prior Publication Data
US 2018/0232951 A1 Aug. 16, 2018

Related U.S. Application Data (60) Provisional application No. 62/165,656, filed on May 22, 2015, provisional application No. 62/165,648, filed on May 22, 2015.

(51) Int. Cl.
G05B 15/00 (2006.01)
G06T 19/00 (2011.01)
(Continued)

(52) U.S. Cl.
CPC .............. *G06T 19/003* (2013.01); *A61B 1/01* (2013.01); *A61B 1/2676* (2013.01); *A61B 34/30* (2016.02);
(Continued)

(58) Field of Classification Search
CPC ... A61B 1/01; A61B 1/2676; A61B 2034/301; A61B 34/30; A61B 90/361; G06T 19/00;
(Continued)

(56) References Cited

U.S. PATENT DOCUMENTS 5,056,529 A 10/1991 de Groot
6,558,309 B2 5/2003 Hogendijk et al.
(Continued)

FOREIGN PATENT DOCUMENTS

EP 0 339 799 A2 11/1989
EP 1 459 692 A1 9/2004
(Continued)

OTHER PUBLICATIONS

Luis G. Torres et al, Interactive-rate Motion Planning for Concentric Tube Robots, Jun. 7, 2014 (Year: 2014).*
(Continued)

*Primary Examiner* — Harry Y Oh
(74) *Attorney, Agent, or Firm* — Jenkins, Wilson, Taylor & Hunt, P.A.

(57) ABSTRACT

Systems for controlling concentric tube probes are disclosed. In some examples, the system includes a concentric tube position display interface and a control system. The concentric tube display interface includes a display for displaying visual feedback to a user indicating a position
(Continued)

(and possibly orientation) of a tip of a concentric tube probe and a user input device for receiving user input from the user designating a goal position (and possibly orientation) for the tip of the concentric tube probe. The control system is configured for interactive-rate motion planning of the concentric tube probe by creating, in real-time or near real-time, a motion plan to move the tip of the concentric tube probe to the goal position (and possibly orientation) while avoiding contact by the concentric tube probe with one or more obstacles and for configuring the concentric tube probe as specified by the motion plan.

26 Claims, 8 Drawing Sheets

(51) Int. Cl.
    *A61B 1/01*           (2006.01)
    *A61B 90/00*         (2016.01)
    *A61B 1/267*         (2006.01)
    *A61B 34/30*         (2016.01)

(52) U.S. Cl.
    CPC ............ *A61B 90/361* (2016.02); *G06T 19/00* (2013.01); *A61B 2034/301* (2016.02); *G06T 2210/21* (2013.01); *G06T 2210/41* (2013.01)

(58) Field of Classification Search
    CPC G06T 19/003; G06T 2210/21; G06T 2210/41
    See application file for complete search history.

(56) References Cited

U.S. PATENT DOCUMENTS

| | | |
|---|---|---|
| 6,770,070 B1 | 8/2004 | Balbierz |
| 7,090,683 B2 | 8/2006 | Brock et al. |
| 7,822,458 B2 | 10/2010 | Webster, III et al. |
| 7,883,475 B2 | 2/2011 | Dupont et al. |
| 8,152,756 B2 | 4/2012 | Webster et al. |
| 2002/0029013 A1 | 3/2002 | Paskar |
| 2002/0087048 A1 | 7/2002 | Brock et al. |
| 2002/0120178 A1 | 8/2002 | Tartaglia et al. |
| 2003/0109852 A1 | 6/2003 | Peterson et al. |
| 2003/0114962 A1* | 6/2003 | Niemeyer .......... A61B 1/00149 700/245 |
| 2004/0015151 A1 | 1/2004 | Chambers |
| 2005/0154379 A1 | 7/2005 | McGowan, Sr. et al. |
| 2005/0203413 A1 | 9/2005 | Fichtinger et al. |
| 2007/0016067 A1 | 1/2007 | Webster, III et al. |
| 2009/0156895 A1 | 6/2009 | Higgins et al. |
| 2009/0171271 A1 | 7/2009 | Webster et al. |
| 2011/0092810 A1 | 4/2011 | Trovato |
| 2011/0251455 A1 | 10/2011 | Popovic |
| 2011/0270040 A1* | 11/2011 | Popovic ............. A61B 17/3421 600/208 |
| 2011/0306986 A1* | 12/2011 | Lee ....................... B25J 9/1689 606/130 |
| 2012/0029288 A1 | 2/2012 | Greenblatt et al. |
| 2012/0062714 A1 | 3/2012 | Liu et al. |
| 2012/0277763 A1 | 11/2012 | Greenblatt et al. |
| 2013/0172906 A1* | 7/2013 | Olson .................... A61B 34/71 606/130 |
| 2014/0276586 A1 | 9/2014 | Swaney et al. |
| 2015/0080907 A1* | 3/2015 | Herrell .................. A61B 34/30 606/130 |
| 2016/0314710 A1* | 10/2016 | Jarc ....................... G09B 23/285 |
| 2018/0214010 A1 | 8/2018 | Alterovitz et al. |

FOREIGN PATENT DOCUMENTS

| | | |
|---|---|---|
| WO | WO 01/70114 A1 | 9/2001 |
| WO | WO 2007/059233 A2 | 5/2007 |
| WO | WO 2016/191361 A1 | 12/2016 |

OTHER PUBLICATIONS

Notification of Transmittal of the International Search Report and the Written Opinion of the International Searching Authority, or the Declaration for International Application No. PCT/US2016/033762 (dated Sep. 29, 2016).
Notification of Transmittal of the International Search Report and the Written Opinion of the International Searching Authority, or the Declaration for International Application No. PCT/US2016/033767 (dated Sep. 1, 2016).
Torres et al., "Interactive-rate Motion Planning for Concentric Tube Robots," PMC, pp. 1-9 (May 1, 2015).
Notice of Allowance and Fee(s) Due and Examiner-Initiated Interview Summary for U.S. Appl. No. 12/084,979 (dated Dec. 16, 2011).
Final Office Action for U.S. Appl. No. 12/084,979 (dated Aug. 1, 2011).
Non-Final Office Action for U.S. Appl. No. 12/084,979 (dated Dec. 22, 2010).
Restriction and/or Election Requirement for U.S. Appl. No. 12/084,979 (dated Sep. 27, 2010).
Notice of Allowance and Fee(s) Due for U.S. Appl. No. 11/436,995 (dated Jun. 25, 2010).
Non-Final Office Action for U.S. Appl. No. 11/436,995 (dated Sep. 10, 2009).
Restriction and/or Election Requirement for U.S. Appl. No. 11/436,995 (dated Mar. 10, 2009).
Okazawa et al., "Hand-Held Steerable Needle Device," IEEE/ASME Transactions on Mechatronics, vol. 10, No. 3, pp. 285-296 (Jun. 2005).
Alterovitz et al., "Steering Flexible Needles Under Markov Motion Uncertainty," IEEE International Conference on Intelligent Robotics and Systems (IROS), pp. 120-125 (Aug. 2005).
Glozman et al., "Flexible Needle Steering and Optimal Trajectory Planning for Percutaneous Therapies," MICCAI 2004, pp. 137-144 (2004).
Lefrançois et al., "Technical Note: A medical needle drive for the study of interstitial implant mechanics," Medical Engineering & Physics, No. 25, pp. 255-258 (2003).
Ebrahimi et al., "Hand-Held Steerable Needle Device," MICCAI 2003, pp. 223-230 (2003).
DiMaio et al., "Needle Steering and Model-Based Trajectory Planning," MICCAI 2003, pp. 33-40 (2003).
Murray et al., "A Mathematical Introduction to Robotic Manipulation," CRC Press (1994).
"What is a Haptic Device?," 3D Systems, https://www.3dsystems.com/haptics-devices/geomagic-touch-x, pp. 1-4 (2018).
"Sensable Phantom Desktop Haptic Device," Geomagic: The Magic of Making it Simple, pp. 1-3 (Oct. 7, 2012).
Bouguet, "Camera Calibration Toolbox for Matlab," http://www.vision.caltech.edu/bouguetj/calib_doc/, pp. 1-5 (Accessed Nov. 13, 2017).
"American Brain Tumor Association (ABTA)," http://abta.org, pp. 1-2, (Accessed Oct. 21, 2017).
Swaney et al., "Toward Transoral Peripheral Lung Access: Combining Continuum Robots and Steerable Needles," J. Med. Robot. Res., vol. 2, No. 1, pp. 1-9 (Mar. 2017).
Johnson et al., "The ITK Software Guide Book 1: Introduction and Development Guidelines Fourth Edition," pp. 1-888 (Dec. 21, 2017).
American Cancer Society, "Cancer Facts & Figures 2014," American Cancer Society, Tech. Rep., pp. 1-72 (2014).
Azimian et al., "Structurally-Redesigned Concentric-Tube Manipulators with Improved Stability," Proc. IEEE/RSJ Int. Conf. Intelligent Robots and Systems, pp. 2030-2035 (2014).
Burgner et al., "A Telerobotic System for Transnasal Surgery," IEEE Transactions on Mechatronics, vol. 19, No. 3, pp. 996-1006 (2014).
Hendrick et al., "A Multi-Arm Handheld Robotic System for Transurethral Laser Prostate Surgery," IEEE International Conference on Robotics and Automation, pp. 2850-2855 (2014).

(56) References Cited

OTHER PUBLICATIONS

Kim et al., "Optimizing Curvature Sensor Placement for Fast, Accurate Shape Sensing of Continuum Robots," Proc. IEEE Int. Conf. Robotics and Automation, pp. 5374-5379 (2014).

Kim et al., Toward a Solution to the Snapping Problem in a Concentric-Tube Continuum Robot: Grooved Tubes with Anisotrophy, IEEE International Conference on Robotics and Automation, pp. 5871-5876 (2014).

Moyer, "Screen for Lung Cancer: U.S. Preventative Services Task Force Recommendation Statement," Annals of Internal Medicine, vol. 160, No. 5, pp. 330-338 (2014).

Patil et al., "Needle Steering in 3-D via Rapid Replanning," IEEE Trans. Robotics, vol. 30, No. 4, pp. 853-864 (2014).

Ryu et al., "FBG-Based Shape Sensing Tubes for Continuum Robots," Proc. IEEE Int. Conf. Robotics and Automation, pp. 3531-3537 (2014).

Schulman et al., "Motion Planning with Sequential Convex Optimization and Convex Collision Checking," International Journal of Robotics Research, vol. 33, No. 9, pp. 1-22 (2014).

Swensen et al., Torsional Dynamics of Steerable Needles: Modeling and Fluroscopic Guidance, IEEE Transactions on Biomedical Engineering, vol. 61, No. 11, pp. 2707-2717 (2014).

Torabi et al., "Compact Robotically Steerable Image-Guided Instrument for Multi-Adjacent-Point (map) Targeting," IEEE Transactions on Robotics, vol. 30, No. 4, pp. 802-815 (2014).

Torres et al., "Interactive-Rate Motion Planning for Concentric Tube Robots," Proc. IEEE Int. Conf. Robotics and Automation, pp. 1915-1921 (2014).

Xu et al., Kinematic Instability in Concentric-Tube Robots: Modeling and Analysis, IEEE International Conference on Biomedical Robotics and Biomechatronics, pp. 163-168 (2014).

Torres et al., "A Motion Planning Approach to Automatic Obstacle Avoidance during Concentric Tube Robot Teleoperation," Department of Computer Science, University of North Carolina at Chapel Hill, pp. 1-7 (publication date unknown).

Bergeles et al., "Planning Stable Paths for Concentric Tube Robots," Proc. IEEE/RSJ Int. Conf. Intelligent Robots and Systems, pp. 3077-3082 (2013).

Bernardes et al., Robot-Assisted Automatic Insertion of Steerable Needles with Closed-Loop Imaging Feedback and Intraoperative Trajectory Replanning, Mechatronics, vol. 23, pp. 630-645 (2013).

Butler et al., "Robotic neuro-endoscope with concentric tube augmentation," National Institutes of Health, pp. 1-21 (2013).

Gilbert et al., "Concentric Tube Robots: State of the Art and Future Directions," 16th International Symposium on Robotics Research, Springer Tracts in Advanced Robotics, pp. 258-274 (2013).

Lobaton et al., "Continuous Shape Estimation of Continuum Robots Using X-Ray Images," Proc. IEEE Int. Conf. Robotics and Automation, pp. 1-20 (2013).

Rucker et al., "Sliding Mode Control of Steerable Needles," IEEE Transactions on Robotics, vol. 29, pp. 1289-1299 (2013).

Sun et al., "Safe Motion Planning for Imprecise Robotic Manipulators by Minimizing Probability of Collision," Proc. Int. Symp. Robotics Research, pp. 1-16 (2013).

Swaney, et al., "A Flexure-Based Steerable Needle: High Curvature With Reduced Tissue Damage," IEEE Trans Biomed Eng., vol. 60, No. 4, pp. 1-10 (2013).

Xu et al., "Position Control of Concentric-Tube Continuum Robots Using a Modified Jacobian-Based Approach," IEEE Int. Conf. Robotics and Automation, pp. 5793-5798 (2013).

Yu et al., "Design, Calibration and Preliminary Testing of a Robotic Telemanipulator for OCT Guided Retinal Surgery," IEEE International Conference on Robotics and Automation, pp. 225-231 (2013).

Butler et al., "Robotic Neuroendoscope with Concentric Tube Augmentation," IEEE/RSJ International Conference on Intelligent Robots and Systems, pp. 1-21 (2012).

Dragan et al., "Formalizing Assistive Teleoperation," Proc. Robotics: Science and Systems, pp. 1-9 (2012).

Gosline et al, "Metal MEMS Tools for Beating-Heart Tissue Removal," IEEE Int. Conf. Robotics and Automation, pp. 1-20 (2013).

Gosline et al., "Percutaneous Intracardiac Beating-Heart Surgery Using Metal Mems Tissue Approximation Tools," International Journal of Robotics Research, vol. 31, No. 9, pp. 1081-1093 (2012).

Hauser, "Recognition, Prediction, and Planning for Assisted Teleoperation of Freeform Tasks," Proc. Robotics: Science and Systems, pp. 1-8 (2012).

Krimsky et al., "Bronchoscopy and the Peripheral Nodule in the Age of Lung Cancer Screening and Targeted Therapies," Current Respiratory Care Reports, vol. 1, No. 1, pp. 67-71 (2012).

Majewicz et al., Behavior of Tip-Steerable Needles in Ex Vivo and In Vivo Tissue, IEEE Transactions on Biomedical Engineering, vol. 59, No. 10, pp. 2705-2715 (2012).

Memoli et al., "Meta-Analysis of Guided Bronchoscopy for the Evaluation of the Pulmonary Nodule," Chest, vol. 142, No. 2, pp. 385-393 (2012).

Pan et al., "FCL: A General Purpose Library for Collison and Proximity Queries," Proc. IEEE Int. Conf. Robotics and Automation, pp. 3859-3866 (2012).

Rosell et al., "Motion Planning for the Virtual Bronchoscopy," IEEE Int. Conf. Robotics and Automation, pp. 2932-2937 (2012).

Şucan et al., "The Open Motion Planning Library," IEEE Robotics and Automation Magazine, http://ompl.kavrakilab.org, vol. 19, No. 4, pp. 72-82 (2012).

Swaney et al., "Design of a Quadramanual Robot for a Single-Nostril Skull Base Surgery," ASME Dynamic Systems and Control, pp. 1-7 (2012).

Torres et al., "Task-Oriented Design of Concentric Tube Robots Using Mechanics-Based Models," IEEE/RSJ International Conference on Intelligent Robots and Systems, pp. 4449-4455 (2012).

Veran Medical Technologies, "SPiN Drive," http://www.veranmedical.com/spin-system/ pp. 1-9 (2012).

Zucker et al., "CHOMP: Convariant Hamiltonian Optimization for Motion Planning," Int. J. Robotics Research, vol. 32, No. 9, pp. 1-45 (2012).

Burgner et al., "A Bimanual Teleoperated System for Endonasal Skull Base Surgery," Proc. IEEE/RSJ Int. Cof. Intelligent Robots and Systems, pp. 2517-2523 (2011).

Cowan et al., "Robotic Needle Steering: Design, Modeling, Planning and Image Guidance," Surgical Robotics: System Applications and Visions, Springer, ch. 23, pp. 557-582 (2011).

Kalakrishnan et al., "STOMP: Stochastic Trajectory Optimization for Motion Planning," IEEE Int. Conf. Robotics and Automation, pp. 1-6 (2011).

Karaman et al., "Sampling-Based Algorithms for Optimal Motion Planning," Int. J. Robotics Research, vol. 30, No. 7, pp. 1-76 (2011).

Lock et al., "Friction Modeling in Concentric Tube Reports," Proc. IEEE Conf. Robotics and Automation, pp. 1-28 (2011).

Reed et al., "Robot-Assisted Needle Steering," IEEE Robotics and Automation Magazine, vol. 18, No. 4, pp. 35-46 (2011).

Rucker, "The Mechanics of Continuum Robots: Model-Based Sensing and Control," Ph.D. dissertation, Vanderbilt University, pp. 1-196 (2011).

Seiler et al., "Using Lie Group Symmetries for Fast Corrective Motion Planning," Int. J. Robotics Research, vol. 31, No. 2, pp. 151-166 (2011).

Torres et al., "Motion Planning for Concentric Tube Robots Using Mechanics-Based Models," Proc. IEEE/RSJ Int. Conf. Intelligent Robots and Systems, pp. 1-18 (2011).

Wiener et al., "Population-based risk of complications following transthoracic needle lung biopsy of a pulmonary nodule," Annals of Internal Medicine, vol. 155, No. 3, pp. 1-15 (Aug. 2, 2011).

American Cancer Society, "Cancer Facts & Figures 2010," American Cancer Society, Tech Rep., pp. 1-68 (2010).

Dupont et al., "Design and Control of Concentric-Tube Robots," IEEE Transactions on Roboticss, vol. 26, No. 2, pp. 209-225 (2010).

Lock et al., "Quasistatic Modeling of Concentric Tube Robots with External Loads," Proc. IEEE/RSJ Int. Conf. Intelligent Robots and Systems, pp. 1-24 (2010).

Lyons et al., "Planning Active Cannula Configurations Through Tubular Anatomy," IEEE International Conference on Robotics and Automation, pp. 2082-2087 (2010).

(56) References Cited

OTHER PUBLICATIONS

Park et al., "The Path-of-Probability Algorithm for Steering and Feedback Control of Flexible Needles," Int. J. Robotics Research, vol. 29, No. 7, pp. 813-830 (2010).
Patil et al., "Interactive Motion Planning for Steerable Needles in 3D Environments with Obstacles," Proc. IEEE RAS/EMBS Int. Conf. Biomedical Robotics and Biomechatronics, pp. 893-899 (2010).
Rucker et al., "A Geometrically Exact Model for Externally Loaded Concentric Tube Continuum Robots," IEEE Transactions on Robotics, vol. 26, No. 5, pp. 769-780 (2010).
SuperDimension, "SuperDimension i-Logic System," http://www.superdimension.com pp. 1-3 (2010).
Webster III et al., "Design and Kinematic Modeling of Constant Curvature Continuum Robots: A Review," International Journal of Robotics Research, vol. 29, No. 13, pp. 1661-1683 (2010).
Dupont et al., "Torsional Kinematic Model for Concentric Tube Robots," IEEE Int. Conf. Robotics and Automation, pp. 1-25 (2009).
Hauser et al., "Feedback Control for Steering Needles Through 3D Deformable Tissue Using Helical Paths," Robotics: Science and Systems, pp. 1-23 (2009).
Horner, et al., "SEER Cancer Statistics Review, 1975-2006, National Cancer Institute. Bethesda, MD," http://seer.cancer.gov/csr/, pp. 1-5 (2009).
Kothary et al., "Computed Tomography-Guided Percutaneous Needle Biopsy of Pulmonary Nodules: Impact of Nodule Size on Diagnostic Accuracy," Clincial Lung Cancer, vol. 10, No. 5, pp. 360-363 (2009).
Lyons et al., "Motion Planning for Active Cannulas," Proc. IEEE/RSJ Int. Conf. Intelligent Robots and Systems, pp. 1-6 (2009).
Minhas et al., "Testing of Neurosurgical Needle Steering via Duty-Cycled Spinning in Brain Tissue in Vitro," International Conference of the IEEE Engineering in Medicine and Biology Society, pp. 258-261 (2009).
Rucker et al., "Parsimonious Evaluation of Concentric-Tube Continuum Robot Equilibrium Conformation," IEEE Trans. Biomedical Engineering, vol. 56, No. 9, pp. 2308-2311 (2009).
Trovato et al., "Collison-Free 6D Non-Holonomic Planning for Nested Cannulas," Proc. SPIE Medical Imaging, vol. 7261 pp. 1-9 (2009).
Webster III et al., "Mechanics of Precurved-Tube Continuum Robots," IEEE Trans. Robotics, vol. 25, No. 1, pp. 67-78 (2009).
Krishna et al., "Minimally Invasive Techniques for the Diagnosis of Peripheral Pulmonary Nodules," Current Opinion in Pulmonary Medicine, vol. 14, pp. 282-286 (2008).
Merritt et al., "Image-Guided Bronchoscopy for Peripheral Lung Lesions: A Phantom Study," CHEST Journal, vol. 134, No. 5, pp. 1017-1026 (2008).
Abolhassani et al., "Needle Insertion Into Soft Tissue: A Survey," Medical Engineering & Physics, vol. 29, No. 4, pp. 413-431 (2007).
Eberhardt et al., "Electromagnetic Navigation Diagnostic Bronchoscopy in Peripheral Lung Lesions," Chest, vol. 131, No. 6, pp. 1800-1805 (2007).
Makris et al., "Electromagnetic Navigation Diagnostic Bronchoscopy for Small Peripheral Lung Lesions," The European Respiratory Journal, vol. 29, No. 6, pp. 1187-1192 (2007).
Minhas et al., "Modeling of Needle Steering via Duty-Cycled Spinning," Proc. Int. Conf. IEEE Engineering in Medicine and Biology Society, pp. 2756-2759 (2007).
Zucker et al., "Multipartite RRTs for Rapid Replanning in Dynamic Environments," Proc. IEEE Int. Conf. Robotics and Automation, pp. 1-8 (2007).
Gildea et al., "Electromagnetic Navigation Diagnostic Bronchoscopy: A Prospective Study," American Journal of Respiratory and Critical Care Medicine, vol. 174, No. 9, pp. 982-989 (2006).
LaValle, "Planning Alogorithms," Cambridge, U.K.: Cambridge University Press, pp. 1-512 (2006).
Sears et al., "A Steerable Needle Technology Using Curved Concentric Tubes," IEEE/RSJ International Conference on Intelligent Robots and Systems, pp. 2850-2856 (2006).
The International Early Lung Cancer Action Program Investigators, "Survival of Patients with Stage I Lung Cancer Detected on CT Screening," The New England Journal of Medicine, vol. 335, No. 17, pp. 1763-1771 (2006).
Van Den Berg, "Anytime Path Planning and Replanning in Dynamic Environments," IEEE Int. Conf. Robotics and Automation, pp. 1-6 (2006).
Webster III et al., "Nonholonomic Modeling of Needle Steering," The International Journal of Robotics Research, vol. 25, No. 5-6, pp. 509-525 (2006).
Webster et al., "Toward Active Cannulas: Miniature Snake-Like Surgical Robots," IEEE/RSJ International Conference on Intelligent Robots and Systems (IROS), pp. 2857-2863 (2006).
Choset et al., "The Principles of Robot Motion: Theory, Algorithms, and Implementations," MIT Press, pp. 1-150 (2007).
Park et al., "Diffusion-Based Motion Planning for a Nonholonomic Flexible Needle Model," Proc. IEEE Int. Conf. Robotics and Automation, pp. 4611-4616 (2005).
Kiraly et al., "Three-Dimensional Path Planning for Virtual Bronchoscopy," IEEE Trans. Medical Imaging, vol. 23, No. 9, pp. 1365-1379 (2004).
Branicky et al., "RRTs for Nonlinear, Discrete, and Hybrid Planning and Control," Proc. IEEE Conf. Decision and Control, pp. 657-663 (2003).
Lien et al., "A General Framework for Sampling on the Medical Axis of the Free Space," IEEE Int. Conf. Robotics and Automation, pp. 4439-4444 (2003).
Bruce et al., "Real-Time Randomized Path Planning for Robot Navigation," Proc. IEEE/RSJ Int. Conf. Intelligent Robots and Systems, pp. 1-6 (2002).
Stachniss et al., "An Integrated Approach to Goal-Directed Obstacle Avoidance Under Dynamic Constraints for Dynamic Environments," Proc. IEEE/RSJ Int. Conf. Intelligent Robots and Systems, vol. 1, pp. 1-6 (2002).
LaValle et al., "Rapidly-Exploring Random Trees: Progress and Prospects," Algorithmic and Computational Robotics: New Directions, pp. 293-308 (2001).
Baaklini et al., "Diagnostic Yield of Fiberoptic Bronchoscopy in Evaluating Solitary Pulmonary Nodules," CHEST Journal, vol. 117, No. 4, pp. 1049-1054 (2000).
Larsen et al., "Fast Proximity Queries with Swept Sphere Volumes," Proc. IEEE Int. Conf. Robotics and Automation, pp. 1-32 (2000).
Miyazawa, "History of the Flexible Bronchoscope," Progress in Respiratory Research: Interventional Bronchoscopy: Basel: Krager, pp. 16-21 (2000).
Brin, "Near Neighbor Search in Large Metric Spaces," Proc. 21st Conf. on Vry Large Databases, pp. 574-584 (1995).
Perlmutt et al., "Percutaneous Transthoracic Needle Aspiration: A Review," American Journal of Roentgenology, vol. 152, pp. 451-455 (1989).
Nakamura et al., "Inverse Kinematic Solutions with Singularity Robustness for Robot Manipulator Control," J. Dynamic Systems, Measurement, and Control, vol. 108, pp. 163-171 (1986).
Wampler, "Manipulator Inverse Kinematic Solutions Based on Vector Formulations and Damped Least-Squares Methods," IEEE Trans. Systems, Man and Cybernetics, vol. 16, No. 1, pp. 93-101 (1986).
Hart et al., "A Formal Basis for the Heuristic Determination of Minimum Cost Paths," IEEE Trans. Systems Science and Cybernetics, vol. 4, No. 2, pp. 100-107 (1968).
Non-Final Office Action for U.S. Appl. No. 15/576,147 (dated Feb. 3, 2020).
Restriction and/or Election Requirement for U.S. Appl. No. 15/576,147 (dated Dec. 2, 2019).
Notice of Allowance and Fee(s) Due for U.S. Appl. No. 15/576,147 (dated Jun. 4, 2020).

\* cited by examiner

METHODS, SYSTEMS, AND COMPUTER READABLE MEDIA FOR CONTROLLING A CONCENTRIC TUBE PROBE

PRIORITY CLAIM

This application claims the benefit of U.S. Provisional Application Ser. No. 62/165,656, filed May 22, 2015, the disclosure of which is incorporated herein by reference in its entirety. This application claims the benefit of U.S. Provisional Application Ser. No. 62/165,648, filed May 22, 2015, the disclosure of which is incorporated herein by reference in its entirety.

GOVERNMENT INTEREST

This invention was made with government support under National Institutes of Health under Grant Nos. EB017467 and EB017952 and by the National Science Foundation under Award No. IIS-1149965. The government has certain rights in the invention.

TECHNICAL FIELD

This specification relates generally to systems for interactive-rate motion planning for concentric tube probes.

BACKGROUND

Concentric tube probes may enable new, safer minimally invasive surgical procedures by moving along curved paths to reach difficult-to-reach sites in a patient's anatomy. Operating these devices is challenging due to their complex, unintuitive kinematics and the need to avoid certain structures in the anatomy. Accordingly, there exists a need for interactive-rate motion planning for concentric tube probes.

SUMMARY

A system for controlling a concentric tube probe includes a concentric tube position (and possibly orientation) display interface and a control system. The concentric tube display interface includes a display for displaying visual feedback to a user indicating a position (and possibly orientation) of a tip of a concentric tube probe and a user input device for receiving user input from the user designating a goal position (and possibly orientation) for the tip of the concentric tube probe. The concentric tube probe can include at least two concentric tubes configured so that translation and rotation of one of the tubes inside another of the tubes creates curvilinear motion of the concentric tube probe. The visual feedback can include position or both position and orientation. Similarly, the goal position can include a goal position or both a goal position and orientation.

The control system is configured for interactive-rate motion planning of the concentric tube probe. The control system can include a system of one or more computers configured for interactive-rate motion planning by virtue of appropriate instructions for the computers stored on one or more computer readable mediums. The control system can include a physical actuation unit for rotating and translating the curved tubes of the concentric tube probe to achieve a configuration specified by the motion plan.

The control system creates, in real-time or near real-time, a motion plan to move the tip of the concentric tube probe to the goal position while avoiding contact by the concentric tube probe with one or more obstacles and for configuring the concentric tube probe as specified by the motion plan. The user input device can continually receive goal positions from the user and the control system can, in response, continually update configurations of the concentric tube probe for collision-free motions to the goal positions. The control system can be configured to cache a plurality of collision-free configurations and motions of the concentric tube probe and the corresponding shapes, positions, and orientations of the concentric tube probe as computed by a kinematic model.

The control system can include a roadmap planner for generating collision-free motions for the concentric tube probe to the goal position by approximating shapes, positions, and orientations of the curved tubes using a kinematic model of the concentric tube probe. The roadmap planner can be configured to, in a preoperative phase, receive a probe specification specifying the shape of the tubes constituting the concentric tube probe, an obstacle specification specifying a location and shape of each of the one or more obstacles, and an insertion pose of the concentric tube probe. The insertion pose can include both the position and the orientation of the concentric tube probe. The roadmap planner can, in the preoperative phase, output a roadmap including a set of configurations of the concentric tube probe and motions between the configurations, wherein the configurations and motions are verified to be collision-free according to the kinematic model, the probe specification, the obstacle specification, and the insertion pose.

The roadmap planner can generate the roadmap using a rapidly-exploring random graph algorithm and can evaluate, for each of a plurality of candidate configurations and motions of the concentric tube probe, whether the candidate configuration or motion satisfies one or more kinematic constraints of the kinematic model and is collision-free according to the obstacle specification. The roadmap planner can be configured to cache a plurality of collision-free configurations and motions of the concentric tube probe and the corresponding shapes, positions, and orientations of the concentric tube probe as computed by a kinematic model. The roadmap planner can register a probe coordinate frame of the concentric tube probe with a target coordinate frame of the obstacle specification.

The goal position can be in proximity of a patient's lungs, and registering the probe coordinate frame with the target coordinate frame can include determining a current breath phase of the patient and registering the probe coordinate frame to the target coordinate frame using the current breath phase and breath phase data associated with the obstacle specification. The roadmap planner can, during an intraoperative phase, respond to a new user-specified goal position by searching the roadmap using a graph search algorithm to produce a collision-free motion plan for the concentric tube probe from a previous position to the new user-specified goal position.

The control system can include a tip error corrector for sensing the position of the tip of the concentric tube probe and moving the tip closer to the goal position. The tip error corrector is configured to receive measurements from a tip position sensing system and use inverse kinematics (IK) to move the tip closer to the goal position.

The concentric tube position display interface can be an augmented reality interface. The user input device of the augmented reality interface can be a 3D mouse. Displaying feedback indicating the position of the tip can include displaying a video feed of the concentric tube probe with an overlaid 3D cursor to indicate an intended goal.

The subject matter described in this specification may be implemented in hardware, software, firmware, or combinations of hardware, software and/or firmware. In some examples, the subject matter described in this specification may be implemented using a non-transitory computer readable medium storing computer executable instructions that when executed by one or more processors of a computer cause the computer to perform operations. Computer readable media suitable for implementing the subject matter described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application specific integrated circuits. In addition, a computer readable medium that implements the subject matter described in this specification may be located on a single device or computing platform or may be distributed across multiple devices or computing platforms.

BRIEF DESCRIPTION OF THE DRAWINGS

The subject matter described herein will now be explained with references to the accompanying drawings of which.

DETAILED DESCRIPTION

This specification describes systems for controlling concentric tube probes. In some examples, the system includes a concentric tube position display interface and a control system. The concentric tube display interface includes a display for displaying visual feedback to a user indicating a position (and possibly orientation) of a tip of a concentric tube probe and a user input device for receiving user input from the user designating a goal position (and possibly orientation) for the tip of the concentric tube probe. The control system is configured for interactive-rate motion planning of the concentric tube probe by creating, in real-time or near real-time, a motion plan to move the tip of the concentric tube probe to the goal position (and possibly orientation) while avoiding contact by the concentric tube probe with one or more obstacles and for configuring the concentric tube probe as specified by the motion plan.

Introduction

Concentric tube probes, sometimes called concentric tube robots, are tentacle-like robotic devices designed for minimally invasive surgery. Their curving ability and small size allow them to reach anatomical sites inaccessible to traditional, straight surgical instruments. Concentric tube probes may enable new, safer surgical access to many sites in the human body, including the skull base, the lungs, and the heart.

These robots can be composed of thin, pre-curved, elastic tubes that are nested within one another. The device's maneuverability is enabled via telescopically inserting and rotating each tube, causing the entire device's shape to change. This powerful shape-changing property also poses a major challenge: unintuitive kinematics determined by mechanical interactions between the device's curved elastic tubes. A physician would therefore find it difficult to safely and accurately guide the robot to perform a surgical task by manually rotating and inserting each tube.

We look to computation to enable intuitive guidance by a physician. Collisions with anatomical obstacles can increase risk to the patient and can bend the device unpredictably, impeding effective control. Requiring a physician to enforce collision avoidance when using a position control interface places a significant burden on the physician. Furthermore, even if the physician successfully steers the tip clear of obstacles, reaching for a given tip position can cause a dramatic change in the robot's shape, potentially causing collision of the robot with anatomical obstacles.

This specification describes a motion planning approach for teleoperation of concentric tube probes that frees the physician to focus on controlling the robot's tip, while an integrated motion planner automatically handles obstacle avoidance along the robot's entire shaft. Motion planning can harness these robots' redundant degrees of freedom in order to curve around obstacles and still reach desired tip positions. This specification describes a motion planner that computes collision-free plans for concentric tube probes at interactive rates. We assume a pre-operative image (e.g., CT scan, MRI, ultrasound) is obtained prior to the procedure, as is common for surgery. From these images anatomical obstacles can be segmented. The interactive-rate motion planner can allow a physician to continuously specify a desired tip location for the concentric tube probe using a 3D mouse (e.g., a SensAble Phantom), and the robot can interactively respond by reaching the desired goal position while ensuring that the entire device shaft avoids anatomical obstacles. The approach can also reduce the error between the commanded goal position and the robot's tip position by using tip position sensing to account for kinematic modeling error.

Achieving interactive-rate motion planning for concentric tube probes is complicated by their kinematics. Accurately evaluating the robot's kinematics is critical for obstacle avoidance. However, accurately estimating the robot's shape requires solving a numerical system that is sufficiently computationally expensive that previous motion planners would be rendered too slow to be used interactively during a procedure that involves obstacle avoidance.

The systems and methods described in this specification achieve interactive rates by creating a motion planner specifically designed for concentric tube probes that mixes precomputation and position control. In the example sampling-based motion planning approach, we begin by pre-computing a roadmap of collision-free paths in the robot's configuration space, and then search for paths on this roadmap during the procedure. We can then use a position control method based on iterative inverse kinematics (IK) to reach user-specified positions not exactly represented in the precomputed roadmap. To link the sampling-based and control approaches, the precomputed roadmap can cache shape information that is computationally expensive to compute online, speeding up the iterative IK. This results in a method that can quickly compute collision-free motion plans to a region of interest, and then can use fast position control to locally guide the robot tip closer to the goal position specified by the physician.

Figure 1:
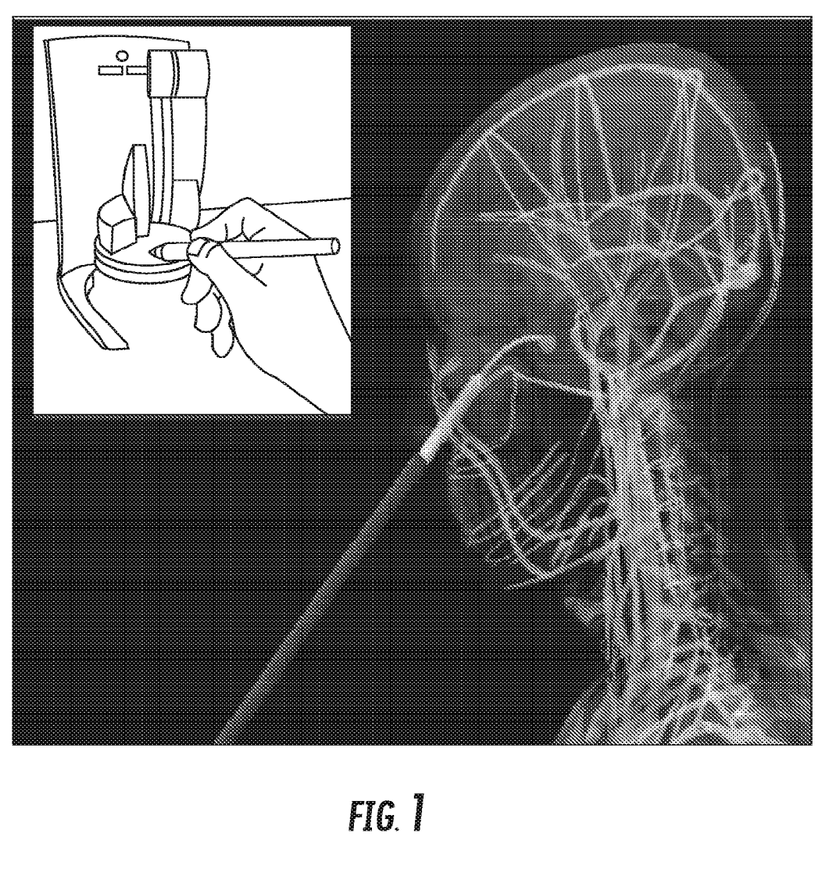
FIG. 1 illustrates a virtual simulation of a concentric tube probe being controlled using a 3D mouse.
Figure 3:
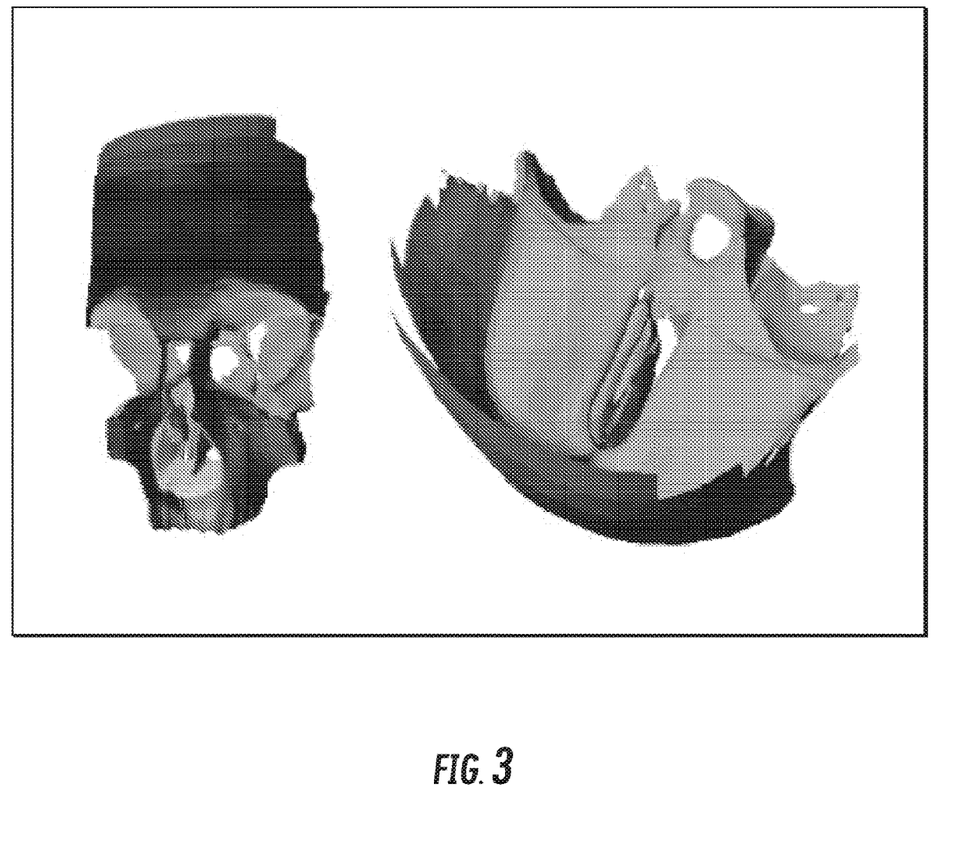
FIG. 3 shows an example 3D model of the nasal cavity and skull base that can be used for collision detection during generation of the roadmap of collision-free concentric tube probe motion plans.
Figure 4:
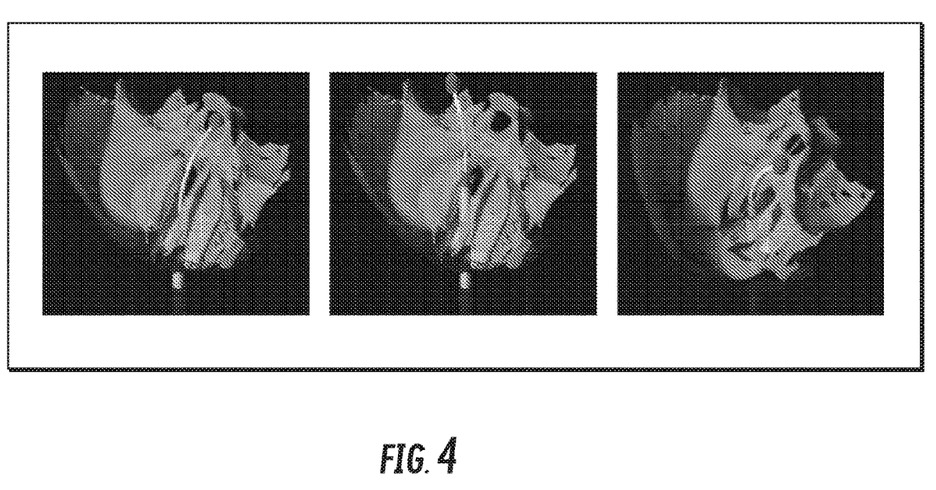
FIG. 4 illustrates three snapshots of an interactive neurosurgical simulation session.
Figure 5:
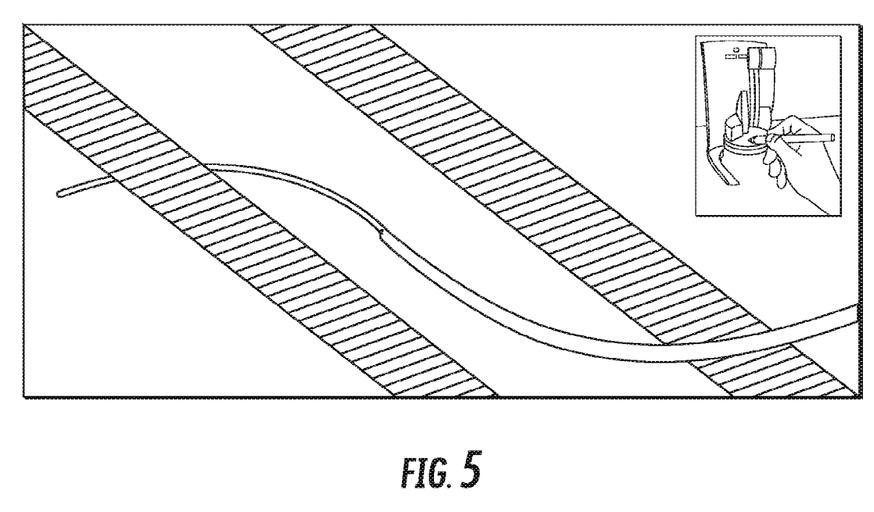
FIG. 5 shows an example concentric tube probe steering between and avoiding two tubular obstacles.

FIG. 1 illustrates a virtual simulation of a concentric tube probe. The concentric tube probe is being controlled with a 3D mouse (e.g., a SensAble Phantom Desktop), as illustrated in the inset. FIG. 3 shows an example 3D model of the nasal cavity and skull base that can be used for collision detection during generation of the roadmap of collision-free concentric tube probe motion plans. FIG. 4 illustrates three snapshots of an interactive neurosurgical simulation session. FIG. 5 shows an example concentric tube probe steering between and avoiding two tubular obstacles. A fast motion planner enables a teleoperated concentric tube probe to maneuver its tip to points specified by a 3D mouse, as shown in the inset of FIG. 5, while automatically avoiding collisions with obstacles along its shaft.

Overview of Approach

Figure 6:
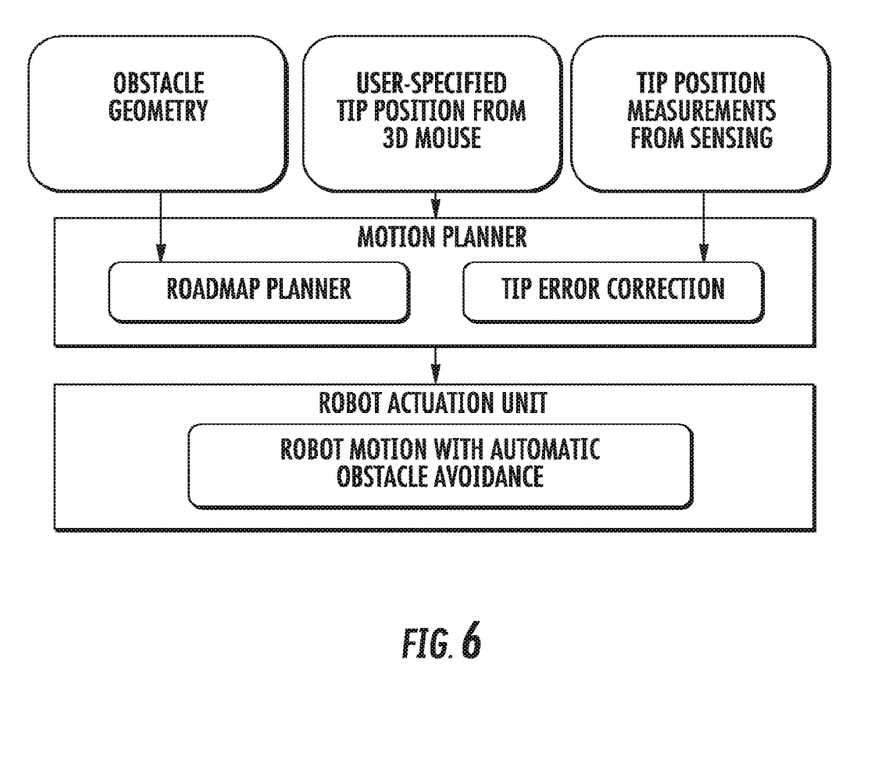
FIG. 6 is a schematic overview of the motion planning approach for concentric tube probe teleoperation with automatic obstacle avoidance.

FIG. 6 is a schematic overview of the motion planning approach for concentric tube probe teleoperation with automatic obstacle avoidance. Before operation, we require a geometrical specification of the anatomical obstacles that must be avoided by the concentric tube probe during the procedure. The obstacles O can be specified using polygonal meshes and can be obtained by segmenting volumetric medical images (e.g., CT scans) either manually or using automatic segmentation software.

During operation, the user repeatedly specifies a new goal position $x_{goal}$ (possibly including orientation) for the concentric tube probe to reach. The robot immediately responds by moving its tip to reach the latest given goal position while automatically avoiding contact with obstacles. The user specifies the goal positions with a 3D mouse in an augmented reality display that shows a cursor overlaid on a video feed of the surgical site (e.g., from an endoscopic camera). The 3D mouse can specify 3D positions, and in some examples can also specify 3D orientations.

A concentric tube probe can include N telescoping tubes. Each tube i can be curved in an arbitrary manner. The device is inserted at a point $x_{start}$ along a vector $v_{start}$.

Each tube may be (1) inserted or retracted from the previous tube, and (2) axially rotated, yielding 2 degrees of freedom per tube. Hence, the robot's configuration is a 2N dimensional vector $q=(\theta_i, \beta_i: i=1, \ldots, N)$ where $\theta_i$ is the axial angle at the base of the i'th tube and $\beta_i \leq 0$ is the arc-length position of the base of tube i behind the robot insertion point (i.e., $\beta=0$ corresponds to $x_{start}$). The configuration space is $\mathcal{Q} = (S^1)^N \times \mathbb{R}^N$.

For a given configuration $q \in \mathcal{Q}$, we represent the device's shape as a 3D space curve $x(q, s): \mathcal{Q} \times [0,1] \mapsto \mathbb{R}^3$ where $x(q, 0) = x_{start}$ and $x(q, 1)$ is the robot's tip position.

Each time the user provides a new $x_{goal}$, the robot's motion planner computes a collision-free sequence of configurations to guide the robot to the vicinity of $x_{goal}$, and then performs a tip error correction step guided by sensed measurements of the tip position. These steps make up a motion plan Pi, denoted by a sequence of configurations $Pi=(q_1, \ldots, q_n)$, to move the robot from its current configuration $q_1$ to a new configuration $q_n$ such that:

1) the distance between the robot's tip $x(q_n, 1)$ and the goal $x_{goal}$ is
2) each configuration $q_i$ of the motion plan Pi is free of contact with obstacles, and
3) each configuration $q_i$ satisfies the robot's kinematic constraints, which includes limits on tube translations.

To enable interactivity, each plan PI should be computed sufficiently fast. Due to the unmodeled effects (e.g., friction and tube tolerances), there may be some difference between mechanics-based model predictions and the robot's actual shape. Thus, we consider the model's predictions to be an estimate $\hat{x}$ of the robot's true shape x. Accurately reaching desired goal positions while ensuring collision avoidance becomes especially challenging when we only have an approximation $\hat{x}$ of the robot's true shape. We describe further below how we select motion plans that encourage collision avoidance and use sensing to correct tip error.

Methods

The motion planning approach for concentric tube probe teleoperation consists of the following components.

a user interface for specifying desired goal points for the robot to reach.

an integrated motion planner that computes a path that moves the robot as close as possible to the goal while avoiding collisions. The planner has two parts: a roadmap-based planner that generates collision-free paths to the goal's vicinity, and a tip error correction (TEC) that senses the robot's tip position and moves the robot's tip closer to the goal.

a physical concentric tube probe actuation unit that executes the commands computed by the motion planner.

The user can specify goal positions (and possibly orientations) for the robot by pointing and clicking with a 3D user input device (e.g. GEOMAGIC TOUCH X), which allows for input of 3D points and, in some examples, can also provide input of 3D orientation. To facilitate selection of goal positions (and possibly orientations), an augmented reality display can show a video feed of the concentric tube probe with an overlaid 3D cursor as the intended goal. We can register the video camera view with the robot's frame of reference. In clinical settings, we expect to use an endoscopic video camera attached to the robot in a manner such that this registration can be pre-calibrated. The user moves the 3D cursor with the handheld stylus of 3D input device, and clicking the stylus triggers the motion planner to move the robot's tip to the specified goal position (and possibly orientation).

Figure 7:
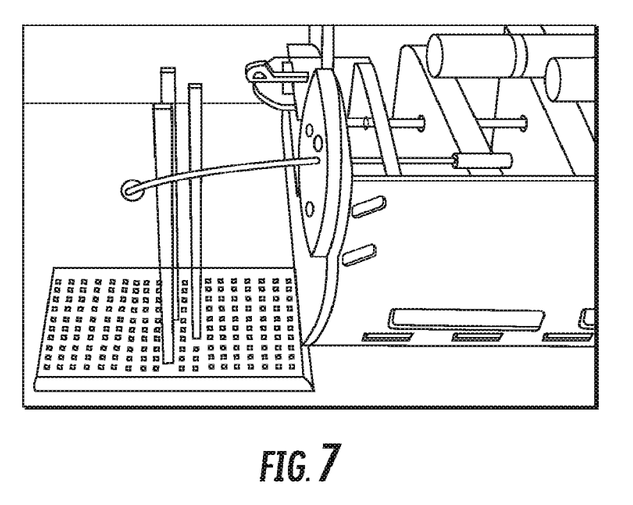
FIG. 7 shows an example augmented reality interface.

FIG. 7 shows an example of the augmented reality interface. The curve is the robot's shape as estimated by the kinematic model, which almost exactly corresponds to the actual tubes in the video feed. A translucent sphere can be used to show the 3D cursor, which the user moves with a 3D mouse to select goal positions (and possibly orientations) for the robot tip.

Figure 2:
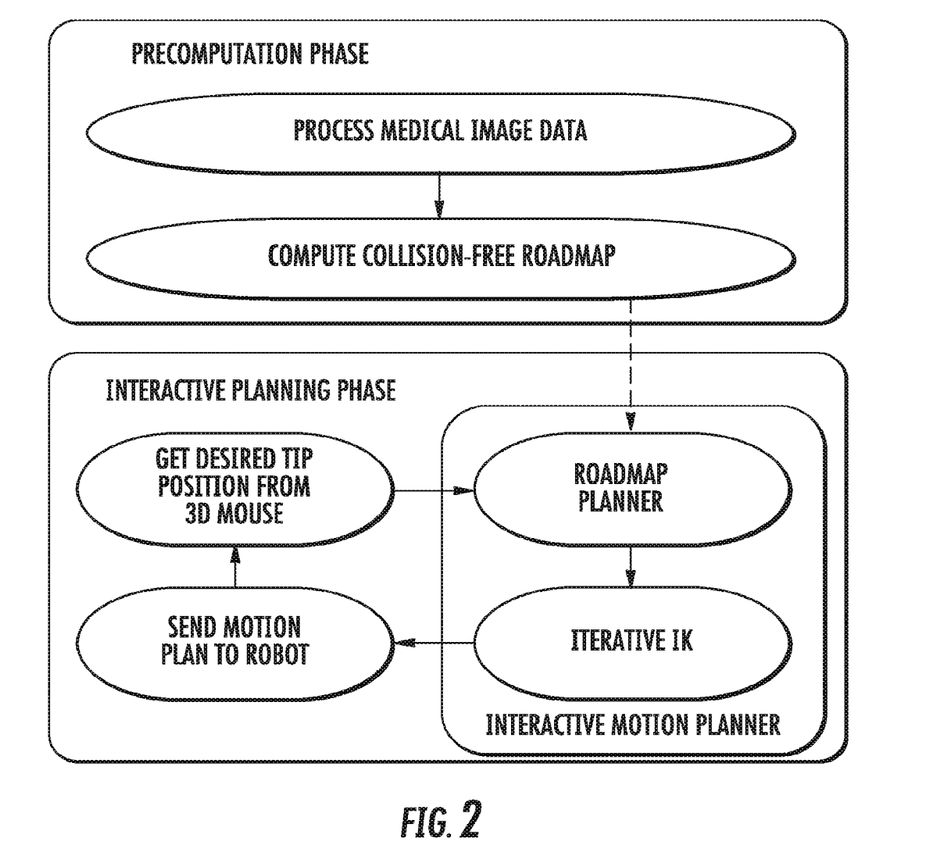
FIG. 2 illustrates the method and the precomputation phase and the interactive planning phase.

We use a motion planner that can generate collision-free paths (as approximated by the kinematic model) for concentric tube probes at interactive rates. The motion planner achieves its speed by separating planning into two phases: a preoperative phase (or precomputation phase) and an intraoperative phase (or interactive planning phase). FIG. 2 illustrates the approach and the two phases.

1) Preoperative Phase: The inputs to the preoperative phase of motion planning are:

the geometry of anatomical obstacles, which can be represented as 3D polygonal surface meshes.
physical specifications of the concentric tube probe.
insertion pose of the concentric tube probe.

The output of the preoperative phase is a discretization of the collision-free subset of the robot's configuration space Q in the form of a roadmap. The roadmap stores a set of configurations and motions between these configurations that have all been verified to be collision-free, according to the kinematic model x̂. The motion connecting two adjacent configurations in the roadmap can be assumed to be linear interpolation. Paths in the roadmap can be represented as sequences of adjacent configurations, which means the roadmap generates piecewise linear motions in configuration space.

The output of the precomputation phase is a precomputed roadmap with cached data that will facilitate interactive planning. We can compute the collision-free roadmap using a rapidly-exploring random graph, or RRG. RRG focuses roadmap construction only on regions of the configuration space that are reachable from the robot's insertion pose. RRG also stores multiple alternative paths between configurations, thus allowing us to select paths that meet application-specific criteria.

The RRG algorithm requires a predicate is_collision_free (q) that evaluates whether the robot satisfies kinematic constraints and is collision-free at configuration q. We can compute this predicate by generating a 3D polygonal mesh on-the-fly of the kinematic model x̂(q, s) and using a collision detection library to check for collisions between the robot's mesh and the anatomical obstacle meshes. For this work we assume the obstacles are described in the robot's coordinate frame, but in some examples, we will need to register to the preoperative volumetric image coordinate system.

We note that the function is_collision_free(q) is approximate because it uses the kinematic model x̂. In order to reduce false negatives in collision detection due to modeling error, we can add padding to the anatomical obstacle representation used in computing is_collision_free(q).

In order to speed up offline roadmap computation and online position control, we store additional information about previous robot shape computations in each node of the roadmap. Computing the robot's shape may require solving for the initial conditions of a boundary value problem. We store the solved initial conditions for each configuration in the roadmap so that they can be used as initial guesses for future shape computations of nearby configurations.

We must also ensure that the roadmap only includes feasible robot configurations. In order to sample only configurations that satisfy the constraints, we can use rejection sampling. We can continually sample from a set of box constraints that tightly contains the true set of valid configurations and reject those samples that violate the constraints.

2) Intraoperative Phase: In the intraoperative phase, the motion planner performs the following steps each time the user specifies a new desired goal position $x_{goal}$.

1) Find the configuration $q_{near\_goal}$ in the roadmap with the minimum predicted tip distance to the goal.

2) Given that the concentric tube probe is currently at configuration $q_{start}$, find the configuration $q_{near\_start}$ in the roadmap that is nearest to $q_{start}$.

3) Use a graph search algorithm (e.g., Dijkstra's shortest path algorithm) to find the optimal sequence of configurations PI* on the roadmap from $q_{near\_start}$ to $q_{near\_goal}$. We will describe below how we define edge costs.

4) Send PI* to the robot for execution.

The roadmap stores multiple alternative collision-free paths between configurations. In some examples, we selected paths that resulted in smooth robot motion by choosing paths that minimized the total distance traveled by the robot's tip. An example alternative is to prioritize collision avoidance over smooth tip motion. In this case, we can select paths based on a metric that considers the robot's clearance from anatomical obstacles. Given a function clear (q) that computes the minimum distance between the robot at configuration q and the anatomical obstacles, we define the cost of the motion connecting configurations $q_1$ and $q_2$ as $$c(q_i, q_2) = \|q_1 - q_2\| \int_0^1 \frac{1}{\text{clear}(q_1 + t(q_2 - q_1))} dt. \quad (1)$$

This function integrates (1/clear(q)) along the linear interpolation between $q_1$ and $q_2$. We can use the reciprocal of the clear function because we want to incur higher cost on a path with smaller robot-obstacle clearance. We can use a collision detection library to compute clear.

We can use Dijkstra's shortest path algorithm using the cost function in Eq. 1 in order to return paths on the roadmap that tend to steer farther away from anatomical obstacles. We can cache these motion costs during precomputation of the collision-free roadmap in order to avoid online evaluation of the expensive clear function.

To reduce errors in practice, we can use measurements from a tip position sensing system combined with iterative inverse kinematics (IK) to "step out" of the precomputed roadmap and toward the specified goal point. To step off the roadmap and move the robot's tip from its sensed position to the goal position, we can use the damped least squares (DLS) IK algorithm. If we do not consider kinematic uncertainty, then we could compute the off-roadmap steps using tip error computed from the kinematic model:

$$\Delta q = \text{DLS\_IK}(x_{goal} - \hat{x}(q,1)). \quad (2)$$

As an example, we incorporate feedback from tip position measurements in order to mitigate the effects of kinematic modeling error. We can take the off-roadmap steps using the tip error measured by the position sensing system:

$$\Delta q = \text{DLS\_IK}(x_{goal} - x_{measured}). \quad (3)$$

We can iteratively sense the position of the robot's tip and adjust the robot's configuration using Eq. 3 until convergence or until we fail to make positive progress toward the goal position. We only perform off-roadmap steps if they are predicted to be collision-free with is_collision_free(q).

CONCLUSION

This specification describes a teleoperated concentric tube probe with integrated motion planning for automatic obstacle avoidance. This specification describes a motion planning method that can compute collision-free plans for concentric tube probes at interactive rates. The planner's speed enables users to continuously move the robot's tip while the planner ensures obstacle avoidance for the robot's shaft. The method derives its speed and accuracy by combining offline precomputation of a collision-free roadmap with online position control. The use of a 3D mouse combined with an augmented reality interface makes the robot's responses to the user's inputs more intuitive. In some examples, the user's spatial reasoning of the surgical site can be improved with a stereoscopic display or visual overlay of surgically relevant anatomical structures. Additionally, force feedback can be used to provide the physician with tactile information about the surroundings of the concentric tube probe.

Figure 8:
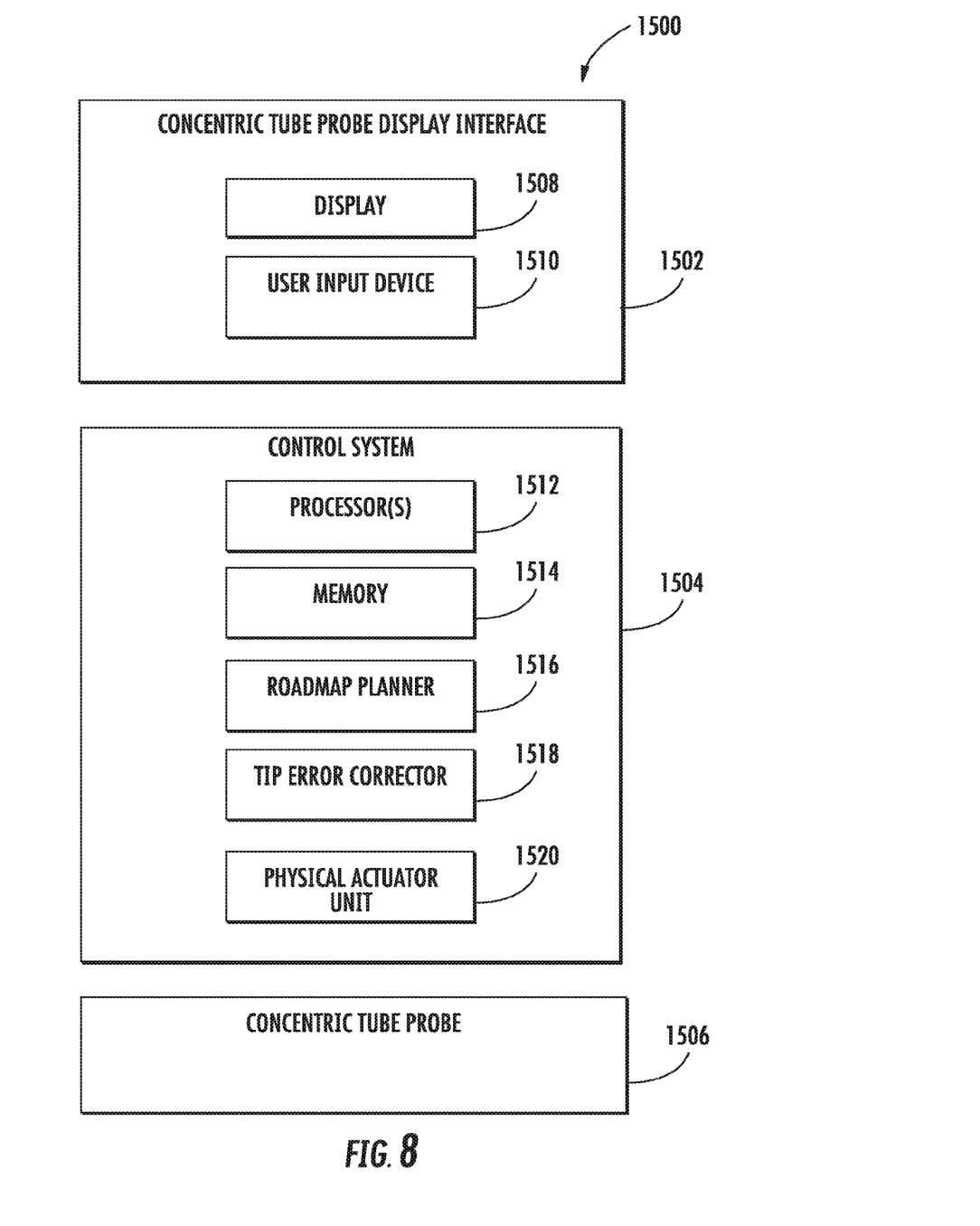
FIG. 8 is a block diagram of an example system for controlling a concentric tube probe.

FIG. 8 is a block diagram of an example system 1500 for controlling a concentric tube probe. System 1500 includes a concentric tube position (and possibly orientation) display interface 1502, a control system 1504, and a concentric tube probe 1506. Concentric tube display interface 1502 includes a display 1508 for displaying visual feedback to a user indicating a position (and possibly orientation) of a tip of concentric tube probe 1506 and a user input device 1510 for receiving user input from the user designating a goal position (and possibly orientation) for the tip of concentric tube probe 1506. Concentric tube probe 1506 can include at least two concentric tubes configured so that translation and rotation of any of the tubes creates curvilinear motion of concentric tube probe 1506. The visual feedback can include position or both position and orientation. Similarly, the goal position can include a goal position or both a goal position and orientation.

Control system 1504 includes one or more processors 1512 and memory 1514 and is configured, by virtue of appropriate programming, for interactive-rate motion planning of concentric tube probe 1506. Control system 1504 can include a physical actuation unit 1520 for rotating and translating the curved tubes of concentric tube probe 1506 to achieve a configuration specified by the motion plan.

Control system 1504 creates, in real-time or near real-time, a motion plan to move the tip of concentric tube probe 1506 to the goal position while avoiding contact by concentric tube probe 1506 with one or more obstacles and configures concentric tube probe 1506 as specified by the motion plan. User input device 1510 can continually receive goal positions from the user and control system 1504 can, in response, continually update configurations of concentric tube probe 1506 for collision-free motions to the goal positions. Control system 1504 can be configured to cache a plurality of collision-free configurations and motions of concentric tube probe 1506 and the corresponding shapes, positions, and orientations of concentric tube probe 1506 as computed by a kinematic model.

Control system 1504 can include a roadmap planner 1516 for generating collision-free motions for concentric tube probe 1506 to the goal position by approximating shapes, positions, and orientations of the curved tubes using a kinematic model of concentric tube probe 1506. Roadmap planner 1516 can be configured to, in a preoperative phase, receive a probe specification specifying the shape of the tubes constituting concentric tube probe 1506, an obstacle specification specifying a location and shape of each of the one or more obstacles, and an insertion pose of concentric tube probe 1506. The insertion pose can include both the position and the orientation of concentric tube probe 1506. Roadmap planner 1516 can, in the preoperative phase, output a roadmap including a set of configurations of concentric tube probe 1506 and motions between the configurations, wherein the configurations and motions are verified to be collision-free according to the kinematic model, the probe specification, the obstacle specification, and the insertion pose.

Roadmap planner 1516 can generate the roadmap using a rapidly-exploring random graph algorithm and can evaluate, for each of a plurality of candidate configurations and motions of concentric tube probe 1506, whether the candidate configuration or motion satisfies one or more kinematic constraints of the kinematic model and is collision-free according to the obstacle specification. Roadmap planner 1516 can be configured to cache a plurality of collision-free configurations and motions of concentric tube probe 1506 and the corresponding shapes, positions, and orientations of concentric tube probe 1506 as computed by a kinematic model. Roadmap planner 1516 can register a probe coordinate frame of concentric tube probe 1506 with a target coordinate frame of the obstacle specification.

The goal position can be in proximity of a patient's lungs, and registering the probe coordinate frame with the target coordinate frame can include determining a current breath phase of the patient and registering the probe coordinate frame to the target coordinate frame using the current breath phase and breath phase data associated with the obstacle specification. Roadmap planner 1516 can, during an intraoperative phase, respond to a new user-specified goal position by searching the roadmap using a graph search algorithm to produce a collision-free motion plan for concentric tube probe 1506 from a previous position to the new user-specified goal position.

Control system 1504 can include a tip error corrector 1518 for sensing the position of the tip of concentric tube probe 1506 and moving the tip closer to the goal position. Tip error corrector 1518 is configured to receive measurements from a tip position sensing system and use inverse kinematics (IK) to move the tip closer to the goal position.

Concentric tube probe display interface 1502 can be an augmented reality interface. User input device 1510 can be a 3D mouse. Displaying feedback indicating the position of the tip can include displaying a video feed of concentric tube probe 1506 with an overlaid 3D cursor to indicate an intended goal.

It is understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system for controlling a concentric tube probe, the system comprising:
a concentric tube position display interface comprising a display for displaying visual feedback to a user indicating a position of a tip of a concentric tube probe and a user input device for receiving user input from the user designating a goal position and optionally orientation for the tip of the concentric tube probe, wherein the concentric tube probe comprises at least two concentric tubes so that translation and rotation of one of the tubes inside another of the tubes creates curvilinear motion of the concentric tube probe; and
a control system for interactive-rate motion planning of the concentric tube probe by creating a motion plan to move the tip of the concentric tube probe to the goal position while avoiding contact by the concentric tube probe with one or more obstacles and for configuring the concentric tube probe as specified by the motion plan;
wherein the user input device continually receives goal positions from the user and wherein the control system updates configurations of the concentric tube probe for collision-free motions to the goal positions;
wherein the control system comprises a roadmap planner for generating collision-free motions for the concentric tube probe to the goal position by approximating shapes, positions, and orientations of the curved tubes using a kinematic model of the concentric tube probe; and
wherein the roadmap planner is configured to, in a preoperative phase, receive a probe specification specifying the shape of each component tube of the concentric tube probe, an obstacle specification specifying a location and shape of each of the one or more obstacles, and an insertion pose of the concentric tube probe, and wherein the roadmap planner is configured to, in the preoperative phase, output a roadmap comprising a set of configurations of the concentric tube probe and motions between the configurations, wherein the configurations and motions are verified to be collision-free according to the kinematic model, the probe specification, the obstacle specification, and the insertion pose.

2. The system of claim 1, wherein the control system is configured to cache a plurality of collision-free configurations of the concentric tube probe.

3. The system of claim 1, wherein the concentric tube position display interface is an augmented reality interface.

4. The system of claim 1, wherein the roadmap planner is configured to generate the roadmap using a rapidly-exploring random graph algorithm and evaluate, for each of a plurality of candidate configurations of the concentric tube probe, whether the candidate configuration satisfies one or more kinematic constraints of the kinematic model and is collision-free according to the obstacle specification.

5. The system of claim 4, wherein the roadmap planner is configured to cache the shapes, positions, and orientations of the concentric tube probe as computed by a kinematic model for the plurality of configurations and motions in the roadmap.

6. The system of claim 1, wherein the roadmap planner is configured to register a probe coordinate frame of the concentric tube probe with a target coordinate frame of the obstacle specification.

7. The system of claim 6, wherein the goal position is in proximity of a patient's lungs, and wherein registering the probe coordinate frame with the target coordinate frame comprises determining a current breath phase of the patient and registering the probe coordinate frame to the target coordinate frame using the current breath phase and breath phase data associated with the obstacle specification.

8. The system of claim 1, wherein the roadmap planner is configured to, during an intraoperative phase, respond to a new user-specified goal position or orientation by searching the roadmap using a graph search algorithm to produce a collision-free motion plan for the concentric tube probe from a previous position and orientation to the new user-specified goal position.

9. The system of claim 1, wherein the control system comprises a tip error corrector for sensing the position of the tip of the concentric tube probe and moving the tip closer to the goal position.

10. The system of claim 9, wherein the tip error corrector is configured to receive measurements from a tip position sensing system and use inverse kinematics (IK) to move the tip closer to the goal position.

11. The system of claim 1, wherein the control system comprises a physical actuation unit for rotating and translating the curved tubes of the concentric tube probe to achieve a configuration specified by the motion plan.

12. The system of claim 1, wherein the user input device comprises a 3D mouse.

13. The system of claim 1, wherein displaying feedback indicating the position of the tip comprises displaying a video feed of the concentric tube probe with an overlaid 3D cursor to indicate an intended goal.

14. A method for controlling a concentric tube probe, the method comprising:
displaying, by a concentric tube position display interface of a system of one or more computers, visual feedback to a user indicating a position of a tip of a concentric tube probe, wherein the concentric tube probe comprises at least two concentric tubes so that translation and rotation of one of the tubes inside another of the tubes creates curvilinear motion of the concentric tube probe;
receiving, by a user input device of the system of one or more computers, user input from the user designating a goal position for the tip of the concentric tube probe;
creating, by the system of one or more computers, a motion plan to move the tip of the concentric tube probe to the goal position while avoiding contact by the concentric tube probe with one or more obstacles; and
configuring, by the system of one or more computers, the concentric tube probe as specified by the motion plan;
continually receiving goal positions from the user and updating configurations of the concentric tube probe for collision-free motions to the goal positions and/or orientations; and
in a preoperative phase:
receiving a probe specification specifying the shape of the concentric tube probe, an obstacle specification specifying a location of each of the one or more obstacles, and an insertion pose of the concentric tube probe; and
outputting a roadmap comprising a set of configurations of the concentric tube probe and motions between the configurations, wherein the configurations are verified to be collision-free according to the kinematic model, the probe specification, the obstacle specification, and the insertion pose.

15. The method of claim 14, comprising caching, for a given position and orientation of the tip and the goal position and/or orientation, a plurality of collision-free configurations of the concentric tube probe to reach the goal position.

16. The method of claim 14, wherein displaying visual feedback comprises displaying an augmented reality interface.

17. The method of claim 14, comprising generating the roadmap using a rapidly-exploring random graph algorithm and evaluating, for each of a plurality of candidate configurations of the concentric tube probe, whether the candidate configuration satisfies one or more kinematic constraints of the kinematic model and is collision-free according to the obstacle specification.

18. The method of claim 14, comprising registering a probe coordinate frame of the concentric tube probe with a target coordinate frame of the obstacle specification.

19. The method of claim 18, wherein the goal position and/or orientation is in proximity of a patient's lungs, and wherein registering the probe coordinate frame with the target coordinate frame comprises determining a current breath phase of the patient and registering the probe coordinate frame to the target coordinate frame using the current breath phase and breath phase data associated with the obstacle specification.

20. The method of claim 14, comprising, during an intraoperative phase, responding to a new user-specified goal position by searching the roadmap using a graph search algorithm to produce a collision-free motion plan for the concentric tube probe from a previous position and orientation to the new user-specified goal position.

21. The method of claim 14, comprising sensing the position of the tip of the concentric tube probe and moving the tip closer to the goal position.

22. The method of claim 21, comprising receiving measurements from a tip position and/or orientation sensing system and using inverse kinematics (IK) to move the tip closer to the goal position.

23. The method of claim 14, wherein the control system comprises a physical actuation unit for rotating and translating the curved tubes of the concentric tube probe to achieve a configuration specified by the motion plan.

24. The method of claim 14, wherein the user input device comprises a 3D mouse.

25. The method of claim 14, wherein displaying feedback indicating the position of the tip comprises displaying a video feed of the concentric tube probe with an overlaid 3D cursor to indicate an intended goal.

26. One or more non-transitory computer readable mediums storing instructions that, when executed by one or more computers, cause the computers to perform operations comprising:

displaying, by a concentric tube position display interface, feedback to a user indicating a position of a tip of a concentric tube probe, wherein the concentric tube probe comprises at least two concentric tubes so that translation and rotation of one of the tubes inside another of the tubes creates curvilinear motion of the concentric tube probe;

receiving, by a user input device, user input from the user designating a goal position and/or orientation for the tip of the concentric tube probe;

creating a motion plan to move the tip of the concentric tube probe to the goal position while avoiding contact by the concentric tube probe with one or more obstacles;

configuring the concentric tube probe as specified by the motion plan;

continually receiving goal positions from the user and updating configurations of the concentric tube probe for collision-free motions to the goal positions and/or orientations; and     in a preoperative phase:

receiving a probe specification specifying the shape of the concentric tube probe, an obstacle specification specifying a location of each of the one or more obstacles, and an insertion pose of the concentric tube probe; and         outputting a roadmap comprising a set of configurations of the concentric tube probe and motions between the configurations, wherein the configurations are verified to be collision-free according to the kinematic model, the probe specification, the obstacle specification, and the insertion pose.

\* \* \* \* \*